United States Patent
Tsuji

(10) Patent No.: US 7,026,931 B2
(45) Date of Patent: Apr. 11, 2006

(54) MICROWAVE SENSOR

(75) Inventor: Masatoshi Tsuji, Ohtsu (JP)

(73) Assignee: Optex Co., Ltd., Shiga (JP)

( * ) Notice: Subject to any disclaimer, the term of this patent is extended or adjusted under 35 U.S.C. 154(b) by 0 days.

(21) Appl. No.: 10/492,949

(22) PCT Filed: Oct. 21, 2002

(86) PCT No.: PCT/JP02/10900

§ 371 (c)(1),
(2), (4) Date: Apr. 19, 2004

(87) PCT Pub. No.: WO03/036327

PCT Pub. Date: May 1, 2003

(65) Prior Publication Data

US 2005/0007124 A1    Jan. 13, 2005

(30) Foreign Application Priority Data

Oct. 19, 2001    (JP)    ............................. 2001-321705

(51) Int. Cl.
*G08B 13/18*    (2006.01)
(52) U.S. Cl. ................. 340/552; 340/435; 340/541; 340/903; 342/27; 342/129
(58) Field of Classification Search ........ 340/552–555, 340/545.2, 541, 903, 435; 342/27, 28, 127, 342/129, 70, 71, 72, 107, 111, 114, 115, 195, 342/118; 324/644; 701/301
See application file for complete search history.

(56) References Cited

U.S. PATENT DOCUMENTS

| 3,932,871 A | * | 1/1976 | Foote ........................ 342/28 |
| 4,003,045 A | * | 1/1977 | Stockdale ................... 367/94 |
| 4,027,303 A | * | 5/1977 | Neuwirth et al. ........... 340/552 |
| 4,647,913 A |   | 3/1987 | Pantus ....................... 340/506 |
| 5,150,099 A | * | 9/1992 | Lienau ....................... 340/552 |
| 6,239,736 B1 | * | 5/2001 | McDonald et al. ......... 342/28 |
| 6,380,882 B1 | * | 4/2002 | Hegnauer ................... 342/28 |

FOREIGN PATENT DOCUMENTS

| EP | 0191510 A1 | 8/1986 |
| JP | 61-215982 | 9/1986 |
| JP | 1-285884 | 11/1989 |
| JP | 8-166449 | 6/1996 |
| JP | 2000-338234 | 12/2000 |

* cited by examiner

*Primary Examiner*—Brent A. Swarthout
(74) *Attorney, Agent, or Firm*—Wenderoth, Lind & Ponack, L.L.P.

(57) ABSTRACT

A sensor has a trigger level that is set in advance in which a distance to a detected object and a signal level of waves reflected from the object are associated. The sensor only dispatches an object detection signal indicating that the detected object is an object to be considered as a detection target having a size larger than a predetermined size when a reflected wave that has a signal level exceeding the trigger level is received.

4 Claims, 3 Drawing Sheets

MICROWAVE SENSOR

TECHNICAL FIELD

The present invention concerns microwave sensors (hereafter "MW sensors") that are active sensors using electromagnetic waves of a frequency lower than visible light. In particular, the present invention relates to improvements in sensing technologies that are effective for identifying a detection object.

BACKGROUND ART

Conventionally, as one form of crime prevention device, MW sensors are known (Japanese Laid-Open Patent Publication No. Hei 7-37176 for example) in which microwaves are transmitted toward a detection area and, when a figure is present in the detection area, the figure (intruder) is detected by receiving the waves (microwaves modulated by the Doppler effect) reflected from that figure.

Moreover, as one type of MW sensor, sensors are known in which a distance to an object is measured using a plurality of microwaves of different frequencies. This type of sensor is set up so that, for example, two microwaves of different frequencies are transmitted toward a detection area, and the phase difference is detected between two IF signals based on the reflected waves of each of these. This phase difference correlates to the distance to a target (a detection target object such as a human figure), with a tendency for the phase difference to be greater for longer distances to the target. In other words, it is possible to measure the distance to the target by obtaining this phase difference. The following is a description concerning an operation for detecting the phase difference in IF signals in this type of sensor.

When the IF signals, which are based on the reflected waves of two microwaves of different frequencies, are sine waves IFout1 and IFout2 (with a phase difference corresponding to the distance to the target) as shown in FIG. 3($a$), the rectangular waves A and B formed from these IF signals are as shown in FIG. 3($b$). It is then possible to measure the distance to the target by detecting the phase difference (the phase difference $\Delta t$ of the rising flank portion of the rectangular waves in the drawing) between the rectangular waves A and B.

Incidentally, when using this type of sensor as a crime prevention sensor, it is preferable that only human figures (intruders) are detected, and that other objects such as small animals are not detected. FIG. 2 shows an example of a relationship between the distance from the sensor when a detected object is a human figure and when the detected object is a small animal (such as a cat), and the signal level of the reflected waves.

As evident in this drawing, when the detection object is a human figure, the signal level is lower when the figure is at positions farther from the sensor. On the other hand, in the case of the detection object being a small animal, when the animal is present at a position an extremely short distance from the sensor, the signal level of the reflected waves is low. This is caused by the directivity of the receiver antenna of the sensor. That is, when a small animal is present at a position an extremely short distance from the sensor, the signal level is low since the receiver antenna receives the reflected waves diagonally from below where directivity is poor. In the case of a small animal being present at a position that is to a certain extent a far distance from the sensor, then, as in the above-described case of a human figure, the signal level is lower at positions farther from the sensor. However, since small animals are of a small size compared to human figures, the signal level of their reflected waves is lower as a whole.

Incidentally, with conventional MW sensors, an object detection signal is transmitted (reported) when a signal level above a preset trigger level is input.

For this reason, it is necessary to set a low trigger level when attempting to also be able to detect intruders that are present at comparatively far distances (a position of 8 m, for example). However, in this case, the probability becomes higher that small animals will be detected. For example, with a trigger level that is set as shown by the broken line in FIG. 2, although intruders that are present at comparatively far distances are detectable, small animals that are present at a position of about 3 m from the sensor also are detected.

Conversely, when setting the trigger level high so as to not detect small animals, intruders that are present at comparatively far distances cannot be detected. For example, with a trigger level that is set as shown by the dot-dash line in FIG. 2, although small animals are not detected, the ability to detect intruders that are present in the vicinity of 7 m from the sensor is lost.

The present invention has been devised giving consideration to this issue, and it is an object therein to provide a MW sensor that detects objects using microwaves with the ability to discriminate the size of a detection object and to offer a MW sensor that can judge whether or not the detection object is of a size that makes it a detection target, and is thus able to avoid false reports.

SUMMARY OF THE INVENTION

In order to achieve the above object, the present invention not only measures the distance to an object based on the microwaves (reflected waves) reflected by the object, but also detects the signal level of the reflected waves, and is able to discriminate the size of the detection object with this information.

Specifically, the present invention relates to a microwave sensor, which transmits a microwave toward a detection target area and, when an object is present in the detection target area, receives a reflected wave of the microwave and measures a distance to the object. The MW sensor is provided with an object detection means that judges a size of the object based on the measured distance to the object and a signal level of the reflected wave from the object, and dispatches an object detection signal only when the size of the object is larger than a predetermined size.

As a specific configuration for carrying out an object detection signal dispatch operation with the object detection means, a trigger level is set in advance that has varied signal level values of reflected waves for which an object detection signal is to be dispatched, the values varying in response to the measured distance to the object, and the object detection means is configured to dispatch an object detection signal only when a reflected wave is received that has a signal level exceeding the trigger level.

With these specified features, it is possible to discriminate the size of the detection object with the distance from the sensor to the object and the signal level of the waves reflected from the object. For example, when applied as a crime prevention sensor, it is possible to judge whether a detection object is a human figure (intruder), which is to be considered a detection target, or whether a detection object is a small animal, which is to be considered a non-detection target, so that the object detection means dispatches an object detection signal only for human bodies, which are detection targets. In this way, it is possible to avoid false reports and to achieve improved sensor reliability.

Furthermore, a specific way of using the microwave sensor is as a crime prevention sensor. That is, an object targeted for detection is a human figure, and the object detection means is configured to dispatch an object detection signal only when the size of the detected object is the same or larger than a human figure.

DETAILED DESCRIPTION OF THE INVENTION

Hereinafter, embodiments of the invention are described with reference to the appended drawings. Description is given here in regard to the case of using a MW sensor as a crime prevention sensor, in which the present invention is applied to a MW sensor that has been made capable of measuring the distance to a detection target object (an intruder or the like) using two microwaves of different frequencies.

Description of Configuration of MW Sensor

Figure 1:
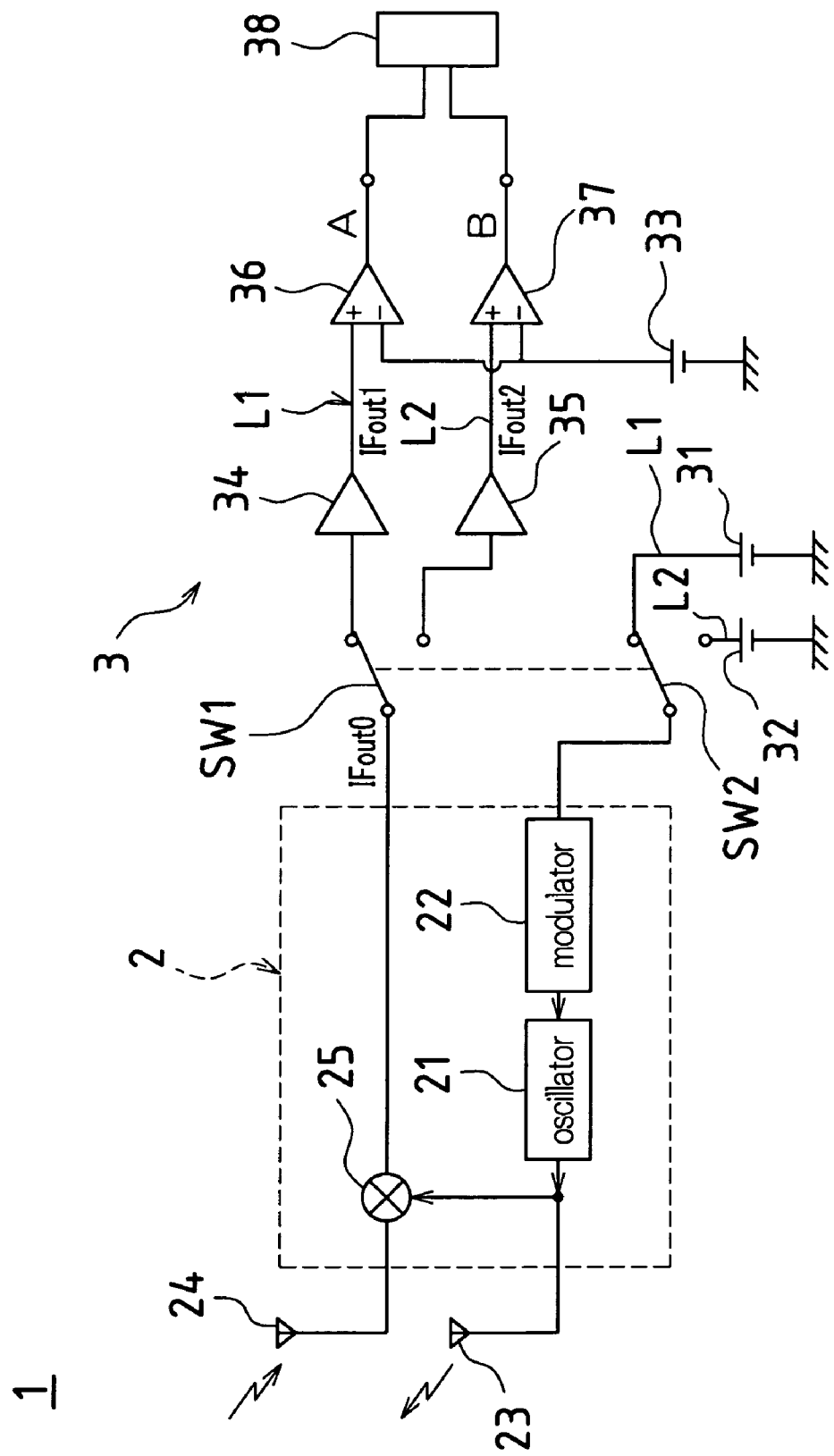
FIG. 1 is a diagram showing a circuit configuration of a MW sensor according to an embodiment of the present invention.

FIG. 1 shows a circuit configuration of a MW sensor 1 according to this embodiment. As shown in FIG. 1, the MW sensor 1 is provided with an RF module 2 and a signal processing portion 3.

The RF module 2 is provided with an oscillator 21 that produces microwaves, a modulator 22 for switching the frequencies of the microwaves produced by the oscillator 21, a transmitter antenna 23 that transmits the microwaves produced by the oscillator 21 toward a detection area, a receiver antenna 24 that receives the reflected waves of the microwaves reflected by an object such as a human figure, and a mixer 25 that mixes and outputs the received microwaves and the voltage waveforms of the oscillator 21. That is, when a human figure or the like is present in the detection area, the microwaves that are transmitted toward the detection area from the transmitter antenna 23 are reflected from that figure and the frequency of the reflected waves is modulated according to the Doppler effect and received by the receiver antenna 24. The received reflected waves are mixed with the voltage waveforms of the oscillator 21 by the mixer 25, and then output from the RF module 2 to the signal processing portion 3 as an IF output signal (IFout0).

On the other hand, the signal processing portion 3 is provided with a first output line L1 and a second output line L2, with each corresponding to one of the microwave frequencies transmitted from the transmitter antenna 23. The lines L1 and L2 are provided with power sources 31, 32, and 33, IF amps 34 and 35, and comparators 36 and 37. An object detection judgment portion 38, which is one of the characteristics of the present embodiment, is arranged as an object detection means at the output side of the comparators 36 and 37.

Each of the IF amps 34 and 35 is connected to the output side of the RF module 2 via a first switch SW1. The first switch SW1 is switchable in that it connects to the first output line L1 when one of the above-mentioned two frequencies of microwaves is sent from the transmitter antenna 23, and connects to the second output line L1 when the other of the two frequencies of microwaves is sent from the transmitter antenna 23. That is, it is configured so that when one of the microwaves is being transmitted, the IF output signal (IFout1) of the reflected waves reflected by a human figure or the like is output to the first output line L1, and when the other microwave is being transmitted, the IF output signal (IFout2) of the reflected waves reflected by a human figure or the like is output to the second output line L2.

The power sources 31 and 32 are connected to the input side of the RF module 2 via a second switch SW2 that is linked to the first switch SW1. The second switch SW2 is also configured so that its connection with respect to the power sources 31 and 32 switches depending on which of the two microwaves is transmitted by the transmitter antenna 23. That is, the microwave frequency for the modulator 22 switches when the second switch SW2 is connected to the power source 31 on the one hand and when it is connected to the power source 32 on the other hand, and in this way the microwave frequency transmitted from the transmitter antenna 23 is configured to be switchable.

In this way, in accordance with the switching operation of the switches SW1 and SW2, a first processing operation in which microwaves of one frequency are transmitted toward the detection area from the transmitter antenna 23 and the IF output signals (IFout1) based on the reflected waves thereof are output to the first output line L1 of the signal processing portion 3 for signal processing at the first output line L1, and a second processing operation in which microwaves of the other frequency are transmitted toward the detection area from the transmitter antenna 23 and the IF output signals (IFout2) based on the reflected waves thereof are output to the second output line L2 of the signal processing portion 3 for signal processing at the second output line L2 are switched with predetermined time intervals (of several milliseconds, for example). Then, the IF output signals that are output from the RF module 2 in these operations are amplified by the IF amps 34 and 35 and the output from the IF amps 34 and 35 are output to the object detection judgment portion 38 after being formed into rectangular waves by the comparators 36 and 37.

Moreover, to describe the above-described processing operations in greater detail, when there is no human figure or the like present in the detection area, the IF frequency of the output signals from the IF amps 34 and 35 are "0," since the frequencies of the microwaves transmitted from the transmitter antenna 23 and the microwaves received by the receiver antenna 24 are equal, and no signals are output from the comparators 36 and 37. In contrast to this, when a human figure or the like is present in the detection area, a change is produced in the waveform of the output signals of the comparators 36 and 37, since the microwaves received by the receiver antenna 24 are modulated with respect to the frequency of the microwaves transmitted from the transmitter antenna 23, and the rectangular waves thereof are output to the object detection judgment portion 38.

Description of Object Detection Judgment Portion 38

The following is a description of the object detection judgment portion 38, which receives output signal waveforms from the comparators 36 and 37. The object detection judgment portion 38 receives output signal waveforms from the comparators 36 and 37 and, based on these, measures the distance to a detection object (a human figure or the like). Furthermore, the object detection judgment portion 38 discriminates the signal level of the waves reflected from the detected object, determines the size of the object based on the above-mentioned measured distance to the detection object and the signal level thereof, and dispatches an object detection signal only when the size of the object is larger than a predetermined size.

Figure 2:
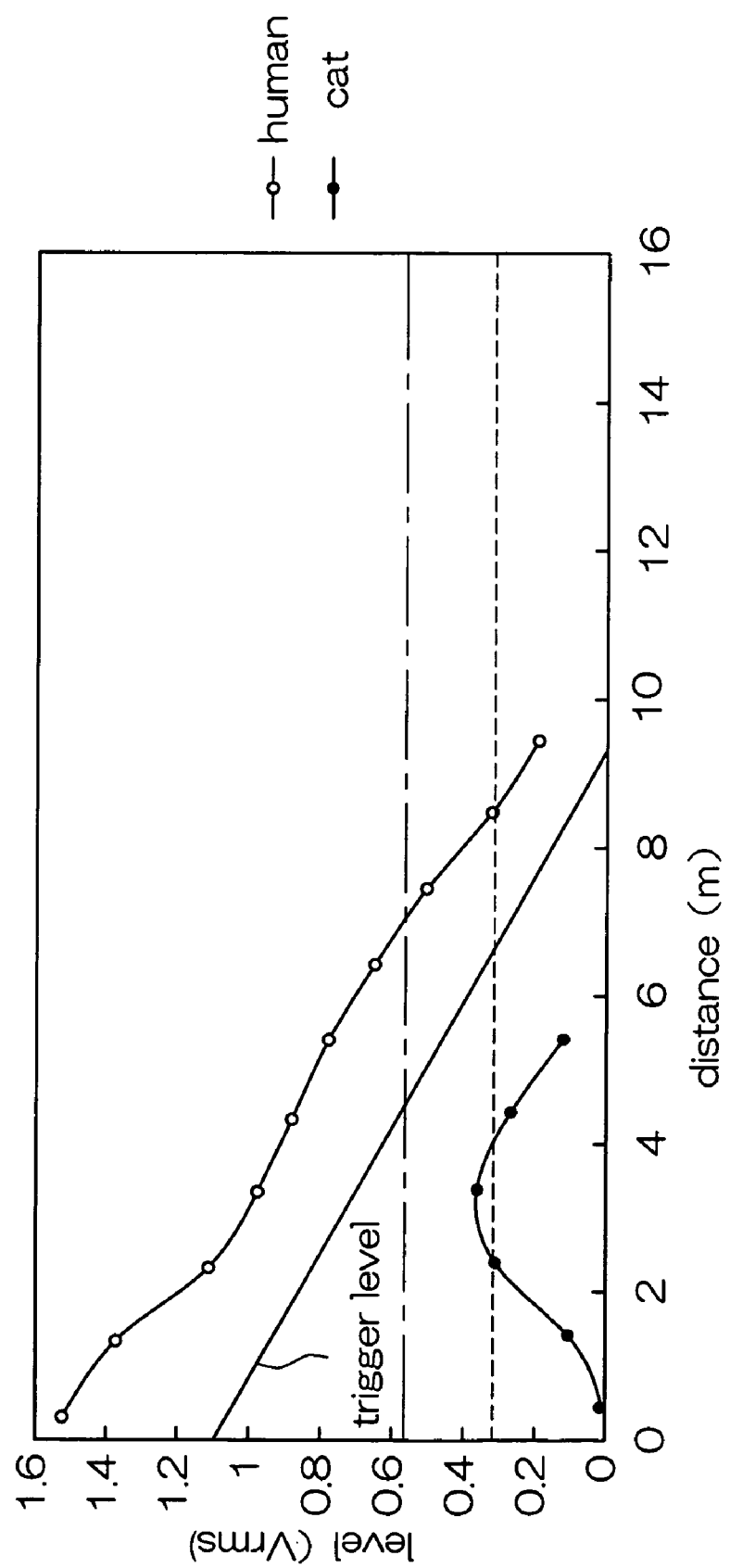
FIG. 2 is a diagram showing the relationship between the distance from the sensor when a detection object is a human figure and when the detection object is a small animal, and the signal level of the reflected waves.
Figure 3:
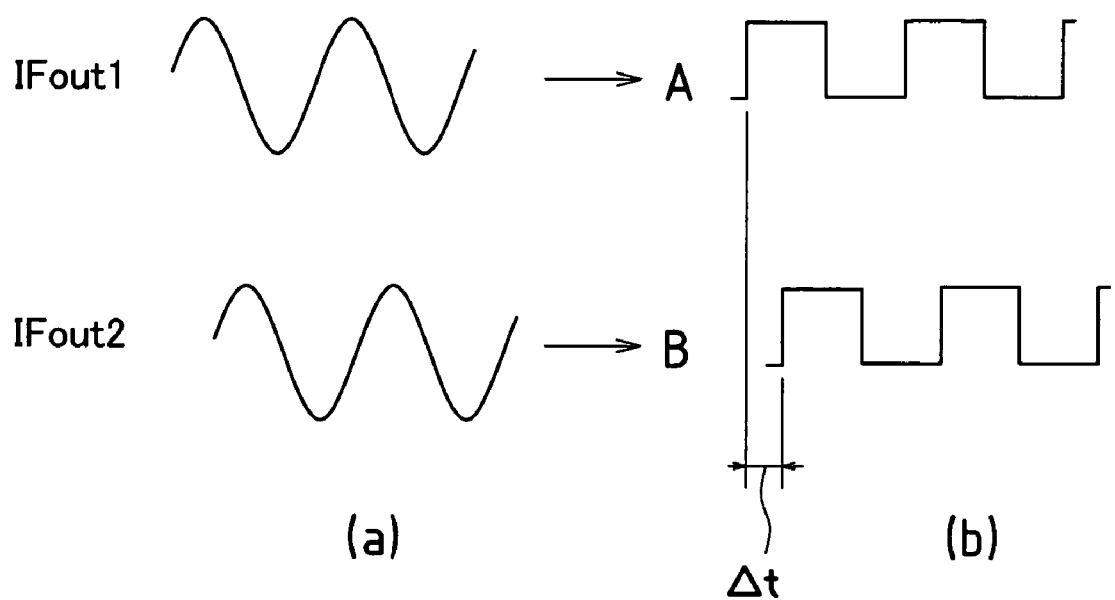
FIG. 3 is a diagram showing a conventional example of IF signals and the rectangular waves obtained from the IF signals.

Specifically, a trigger level is set in advance in which the distance to the object and the signal level of the waves reflected from the object are associated, and an object detection signal is dispatched (reported) by the object detection judgment portion 38 only when there is a condition in which the level of the received reflected waves exceeds the trigger level. As shown by the solid line in FIG. 2, the trigger level is set so that the signal level by which an object detection judgment is made becomes progressively smaller for longer distances to the detection object. It should be noted that the inclination angle of the trigger level is set in accordance with such factors as the installation environment of the sensor and the directivity of the receiver antenna.

Also note that the following relational expression (1) is established between the distance to the object, the size of the object, and the electrical power (signal level) of the received signal. It is possible to determine the size of the object from the distance to the object and the electrical power (signal level) of the received signal by using the expression (1).

$$Pr = \sigma G^2 Pt \lambda / \{(4\pi)^3 d^4\} \qquad \ldots (1)$$

Where Pr is the received electrical power, Pt is the transmitted electrical power, G is antenna gain, λ is wavelength, σ is a radar cross section (object size), d is distance, and R is the load resistance.

By setting the trigger level in this way, when the distance to the object is 4 m, for example, no object detection signal is dispatched as long as the signal level does not exceed 0.6 Vrms. In other words, an object in a position distanced 4 m from the sensor and whose signal level exceeds 0.6 Vrms is judged to be an intruder, and an object detection signal is dispatched in this case. On the other hand, even if an object is in a position distanced 4 m from the sensor, if the object's signal level does not exceed 0.6 Vrms, it is judged to be a small animal, and no object detection signal is dispatched in this case.

As described above, in the present embodiment, whether a detection object is a human figure (intruder), which is to be considered a detection target, or whether a detection object is a small animal, which is to be considered a non-detection target, is determined by discriminating the size of the object, and the object detection judgment portion 38 dispatches an object detection signal only when the object is considered a detection target. In this way, it is possible to provide the MW sensor 1 that can avoid false reports and has high reliability.

Other Embodiments

The above embodiment was described with regard to the MW sensor 1 that measures the distance to a detection object using two microwaves of different frequencies. The present invention is not limited to this, and it is also possible to measure the distance to a detection object using microwaves with three or more different frequencies. Furthermore, the present invention can also be applied to pulse system and FM-CW system MW sensors.

Moreover, there is no limitation to the above-described trigger level. For example, it is also possible to set a trigger level that has a different inclination to that shown in FIG. 2, or to set a trigger level that has a curved shape or that is bent in some locations.

Furthermore, the MW sensor 1 of the present invention may also be applied in uses other than crime prevention sensors.

INDUSTRIAL APPLICABILITY

As described above, in contrast to an MW sensor that measures the distance to an object using microwaves, a microwave sensor according to the present invention not only measures the distance to that object based on the microwaves reflected by the object, but also detects the signal level of the reflected waves, and is thus superior in that it is able to discriminate the size of the detection object with this information. In this way, it is possible to set in advance the size of objects that are to be considered as detection targets, so that only objects of a specified size are detected, thus achieving improved sensor reliability by being able to avoid false reports. For example, when applied as a crime prevention sensor, it is judged whether a detection object is a human figure (intruder), which is to be considered a detection target, or whether a detection object is a small animal, which is to be considered a non-detection target, so that the object detection means dispatches an object detection signal only when the object is considered a detection target, and can thus be used effectively as a highly reliable MW sensor.

The invention claimed is:

1. A microwave sensor comprising:
    an RF module operable to transmit microwaves of at least two frequencies toward a detection target area, and receive reflected waves of the microwaves if an object is present in the detection target area; and
    object detection means for measuring a distance to the object based on the reflected waves from the object, judging a size of the object based on the measured distance to the object and signal levels of the reflected waves from the object, and dispatching an object detection signal only when the size of the object is larger than a predetermined size indicated by the signal levels of the reflected waves exceeding a trigger level for the measured distance,
    wherein the trigger level decreases linearly as the measured distance to the object increases.

2. The microwave sensor according to claim 1, wherein
    the object targeted for detection is a human figure, and
    said object detection means dispatches the object detection signal only when the size of the object is the same or larger than a human figure.

3. A microwave sensor comprising:
    an RF module operable to transmit microwaves of at least two frequencies toward a detection target area, and receive reflected waves of the microwaves if an object is present in the detection target area; and
    an object detection judgment portion operable to measure a distance to the object based on the reflected waves from the object, judge a size of the object based on the measured distance to the object and signal levels of the reflected waves from the object, and dispatch an object detection signal only when the size of the object is larger than a predetermined size indicated by the signal levels of the reflected waves exceeding a trigger level for the measured distance,
    wherein the trigger level decreases linearly as the measured distance to the object increases.

4. The microwave sensor according to claim 3, wherein the object targeted for detection is a human figure, and
    said detection judgment portion dispatches the object detection signal only when the size of the object is the same or larger than a human figure.

* * * * *